(12) United States Patent
Harvey et al.

(10) Patent No.: US 9,327,279 B2
(45) Date of Patent: May 3, 2016

(54) METHODS FOR THE PRODUCTION OF RENEWABLE DIMETHYL JP10

(75) Inventors: Benjamin G. Harvey, Ridgecrest, CA (US); Heather A. Meylemans, Ridgecrest, CA (US); Roxanne L. Quintana, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 818 days.

(21) Appl. No.: 13/604,115

(22) Filed: Sep. 5, 2012

(65) Prior Publication Data

US 2015/0011807 A1    Jan. 8, 2015

Related U.S. Application Data

(63) Continuation-in-part of application No. 12/511,796, filed on Jul. 29, 2009, now Pat. No. 8,395,007.

(60) Provisional application No. 61/531,970, filed on Sep. 7, 2011.

(51) Int. Cl.

| | |
|---|---|
| *C10L 1/16* | (2006.01) |
| *C07C 1/22* | (2006.01) |
| *C07C 1/24* | (2006.01) |
| *C07C 13/32* | (2006.01) |
| *C07C 9/00* | (2006.01) |
| *B01J 31/18* | (2006.01) |
| *B01J 31/14* | (2006.01) |
| *B01J 31/22* | (2006.01) |
| *C10G 45/00* | (2006.01) |
| *C10G 50/00* | (2006.01) |
| *C10G 69/12* | (2006.01) |
| *C10L 1/08* | (2006.01) |
| *C10G 45/32* | (2006.01) |
| *C10G 45/58* | (2006.01) |
| *C10G 65/04* | (2006.01) |
| *C10G 65/06* | (2006.01) |
| *C10L 1/04* | (2006.01) |
| *C10L 1/06* | (2006.01) |
| *C10G 3/00* | (2006.01) |

(52) U.S. Cl.
CPC ............. *B01J 31/189* (2013.01); *B01J 31/143* (2013.01); *B01J 31/2273* (2013.01); *B01J 31/2278* (2013.01); *B01J 31/2295* (2013.01); *C10G 3/42* (2013.01); *C10G 45/00* (2013.01); *C10G 45/32* (2013.01); *C10G 45/58* (2013.01); *C10G 50/00* (2013.01); *C10G 65/043* (2013.01); *C10G 65/06* (2013.01); *C10G 69/126* (2013.01); *C10L 1/04* (2013.01); *C10L 1/06* (2013.01); *C10L 1/08* (2013.01); *B01J 2531/48* (2013.01); *C10G 2300/1011* (2013.01); *C10G 2300/1092* (2013.01); *C10G 2300/302* (2013.01); *C10G 2300/308* (2013.01); *C10G 2300/44* (2013.01); *C10G 2300/703* (2013.01); *C10G 2400/02* (2013.01); *C10G 2400/04* (2013.01); *C10G 2400/08* (2013.01); *C10G 2400/22* (2013.01); *Y02E 50/13* (2013.01); *Y02P 30/20* (2015.11)

(58) Field of Classification Search
None
See application file for complete search history.

(56) References Cited

U.S. PATENT DOCUMENTS

| | | | | |
|---|---|---|---|---|
| 3,002,829 | A * | 10/1961 | Kolfenbach et al. | 585/22 |
| 3,381,046 | A * | 4/1968 | Cohen et al. | 585/22 |
| 4,394,528 | A * | 7/1983 | Fisher | 585/14 |
| 5,414,173 | A * | 5/1995 | Garces et al. | 585/357 |

OTHER PUBLICATIONS

Hoye et al. "Some Allylic Substituent Effects in Ring-Closing Metathesis Reactions: Allylic Alcohol Activation", Organic Letters. 1999, vol. 1, No. 7, 1123-1125.*
Kumar et al. AlCl3-catalyzed dimerization of 1,3-cyclopentadiene in the chloroaluminate room temperature ionic liquid, Journal of Molecular Catalysis A: Chemical 208 (2004) 33-37.*
Conrad et al. "Ruthenium-Catalyzed Ring-Closing Metathesis: Recent Advances, Limitations and Opportunities", Current Organic Chemistry, 2006, 10, 185-202.*

* cited by examiner

*Primary Examiner* — In Suk Bullock
*Assistant Examiner* — Ali Z Fadhel
(74) *Attorney, Agent, or Firm* — Charlene A. Haley (57) ABSTRACT

A highly efficient method for the conversion of a natural product into the high density fuel RJ-4 with concomitant evolution of isobutylene for conversion to fuels and polymers, more specifically, embodiments of the invention relate to efficient methods for the conversion of the renewable, linear terpene alcohol, linalool into a drop-in, high density fuel suitable for ramjet or missile propulsion.

11 Claims, 9 Drawing Sheets

FIGURE 9

METHODS FOR THE PRODUCTION OF RENEWABLE DIMETHYL JP10

CROSS-REFERENCE TO RELATED APPLICATIONS

This is a non-provisional patent application of, claiming the benefit of, parent application Ser. No. 61/531,970 filed on Sep. 7, 2011, and is a continuation-in-part of, claiming the benefit of, parent application Ser. No. 12/511,796 filed on Jul. 29, 2009, now U.S. Pat. No. 8,395,007 whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a highly efficient method for the conversion of a natural product into the high density fuel RJ-4 with concomitant evolution of isobutylene for conversion to fuels and polymers.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to a highly efficient method for the conversion of a natural product into the high density fuel RJ-4 with concomitant evolution of isobutylene for conversion to fuels and polymers.

More specifically, embodiments of the invention relate to efficient methods for the conversion of the renewable, linear terpene alcohol, linalool into a drop-in, high density fuel suitable for ramjet or missile propulsion. In line with Navy goals, these embodiments have the potential to decrease net carbon emissions of various platforms while maintaining optimum performance.

Fuels suitable for missile propulsion have multi-cyclic structures that impart high density while maintaining suitable low temperature viscosity. These fuels are particularly difficult to produce from renewable sources given their stringent requirements. Embodiments of this invention describe a highly efficient method for the conversion of the naturally occurring terpene alcohol, linalool, into the high density fuel RJ-4 which is composed of hydrogenated methylcyclopentadiene dimers. Recent work has shown that terpene alcohols and related molecules can be produced from cellulose with bioengineered organisms. In conjunction with the embodiments of this invention, this will allow for the sustainable and renewable production of a high density fuel from waste biomass. In addition to the production of RJ-4, embodiments of this invention generate isobutylene as a side-product which can be isolated and converted to gasoline, jet fuel, or polymers/elastomers.

The ring closing metathesis (RCM) of linalool to produce 1-methylcyclopent-2-enol and isobutylene using Ru-metathesis catalysts has been demonstrated in the literature. However, previous methods have utilized elevated temperatures, dilute solutions in chloroform, and in general, high catalyst loadings. This is in contrast to embodiments of this invention method which are performed without solvent and at loadings as low as 0.01 mol %.

Embodiments of the invention relate to a method for manufacturing high density fuels including, reacting at least one terpene alcohol with at least one Ru-metathesis catalysts with a solvent or under solvent-free conditions to produce 1-methylcyclopent-2-enol, dehydrating the 1-methylcyclopent-2-enol with at least one heterogeneous dehydration catalyst to produce methylcyclopentediens, thermal dimerizing of the methylcyclopentadienes to produce methylcyclopentadiene dimers, hydrogenating the methylcyclopentadiene dimers with at least one hydrogenation catalyst to produce hydrogenated methylcyclopentadiene dimers, and isomerizing the hydrogenated methylcyclopentadiene dimers with at least one Lewis acid catalyst to produce high density fuels. Other embodiments of the invention relate to a method for producing fuels and/or byproducts including, reacting at least one terpene alcohol with at least one Ru-metathesis catalysts under solvent-free conditions to produce isobutylene, and oligomerizing the isobutylene with at least one oligomerization catalyst to produce at least one of the fuels and/or byproducts selected from the group consisting of gasoline, jet fuel, and polymers/elastomers.

Another aspect of the invention is the high density fuels, gasoline products, jet fuels, polymer/elastomer products, and fuel blends produced either by one or a combination of the methods therein. Another aspect of the invention relates to a method for manufacturing high density fuels including, reacting at least one terpene with at least one Ru-metathesis catalysts with a solvent or under solvent-free conditions to produce 3-methylenecyclopent-1-ene, isomerizing the 3-methylenecyclopent-1-ene with at least one isomerization catalyst to produce methylcyclopentadienes, thermal dimerizing of the methylcyclopentadienes to produce methylcyclopentadiene dimers, hydrogenating the methylcyclopentadiene dimers with at least one hydrogenation catalyst to produce hydrogenated methylcyclopentadiene dimers, and isomerizing the hydrogenated methylcyclopentadiene dimers with at least one Lewis acid catalyst to produce high density fuels.

Embodiments of the invention include at least one terpene alcohol is linalool. Other embodiments include at least one Ru-metathesis catalysts is selected from the group consisting of first generation Grubbs catalyst, second generation Grubbs, Grubbs-Hoveyda catalyst, catalysts with electron withdrawing alkoxides and labile pyridine ligands, and any metathesis catalyst tolerant of alcohols, including heterogeneous metal oxides and polymer supported catalysts. In embodiments, at least one heterogeneous dehydration catalyst is selected from the group consisting of $AlPO_4$, $Al_2O_3$, silica, $MgSO_4$, zeolites, and molecular sieves. In other embodiments, the thermal dimerizing method includes increasing the temperature to accelerate the dimerization of the methylcyclopentadienes to produce methylcyclopentadienes dimers. In other embodiments, the thermnnal dimerizing method includes utilizing room temperature to dimerize the methylcyclopentadienes to produce methylcyclopentadiene dimers.

In embodiments, a Lewis acid catalyst is employed to increase the rate of dimerization of methylcyclopentadienes. In embodiments, at least one hydrogenation catalyst includes at least one of Ni, Pd, Pt, and Cu, either supported or unsupported. In embodiments, at least one Lewis acid catalyst for isomerization of tetrahydrodimethylcyclopentadienes is selected from the group consisting of $AlCl_3$, ionic liquids and salts including $AlCl_4^-$ as the anion, and other homogenous or heterogeneous Lewis acids. In embodiments, the high density fuels is tetrahydrodimethylcyclopentadiene (RJ-4). In other embodiments, at least one oligomerization catalyst is selected from the group consisting of supported polyphosphoric acid, zeolites, metal oxides, cation exchange resins, Lewis acids, and acid clays. In embodiments, the at least one terpene is myrcene (see Scheme 6).

Aspects of the invention relate to a highly efficient method for the conversion of a natural product into the high density fuel RJ-4 with concomitant evolution of isobutylene for conversion to fuels and polymers as shown in Schemes 1 and 2

Scheme 1.

Scheme 2.

The development of techniques for the efficient synthesis of custom fuels and chemicals from sustainable natural feedstocks is of fundamental importance to society as the direct and indirect costs of petroleum use continue to increase. (A. J. Ragauskas, C. K. Williams, B. H. Davison, G. Britovsek, J. Cairney, C. A. Eckert, W. J. Frederick, J. P. Hallet, D. J. Leak, C. L. Liotta, J. R. Mielenz, R. Murphy, R. Templer, T. Tschaplinski, *Science* 2006, 311, 484-489. b) G. W. Huber, S. Iborra, A. Conna, *Chem. Rev.* 2006, 106, 4044-4098. c) J. Hill, *Sust. Agric.* 2009, 125-139). For general transportation fuels, complex mixtures or molecules that have somewhat lower utility than petroleum based analogs may be sufficient, however for specific applications such as jet and missile propulsion, a more selective model that produces molecules with defined and specialized properties is required. Well characterized, single-site catalysis is the basis of elegant synthetic strategies for the production of pure compounds. In particular, ruthenium-based olefin metathesis catalysts are known to catalyze a number of reactions including self-metathesis, cross-metathesis, ring closing metathesis (RCM) and ring opening metathesis polymerization (ROMP). (G. C. Vougioukalakis, R. H. Grubbs, *Chem. Rev.* 2010, 110, 1746-1787; A. H. Hoveyda, A. R. Zhugralin, *Nature* 2007, 450, 243-251. c) R. H. Grubbs, *Angew. Chemie Int'l. Ed* 2006, 45, 3760-3765; R. H. Grubbs, *Tetrahedron* 2004, 60, 7117-7140; C. Samojlowicz, M. Bieniek, K. Grela, *Chem. Rev.* 2009, 109, 3708-3742). This family of catalysts is ubiquitous in the literature and has been used for everything from natural product synthesis to polymer chemistry. (D. E. White, I. C. Stewart, R. H. Gnbbs, B. M. Stoltz, *J. Am. Chem. Soc.* 2008, 130, 810-811; M. Arisawa, A. Nishida, M. Nakagawa, *J. Organomet. Chem.* 2006, 691, 5109-5121; G. O. Wilson, M. M. Caruso, N. T. Reimer, S. R. White, N. R. Sottos, J. S. Moore, *Chem. Mater.* 2008, 20, 3288-3297; R. M. Thomas, R. H. Orubbs, *Macromolecules* 2010, 43, 3705-3709.) The transition of these catalysts to large scale industrial processes has in the past been hindered by their modest turnover numbers and high cost. (M. Ulman, R. H. Grubbs, *J. Org. Chem.* 1999, 64, 7202-7207. b) J. C. Conrad, J. L. Snelgrove, M. D. Eeelman, S. Hall, D. E. Fogg *J. Molec. Catal. A* 2006, 254, 105-110). To overcome these difficulties, catalytic systems need to be developed that can efficiently yield pure products while maintaining low catalyst loadings. In this specification, we detail a ruthenium catalyzed method for the synthesis of dimethyldicyclopentadiene from linalool, a linear terpene alcohol. Recent work in our lab has focused on the conversion of terpenes to high density fuel surrogates. (B. G. Harvey, M. E. Wright, R. L. Quintana *Energy Fuels* 2010, 24, 267-273). Although terpenes are naturally produced by pine trees and a variety of plants, a truly sustainable method may require the utilization of bioengineered microbes to produce specific molecules or families of molecules from waste cellulose. (M. C. Y. Chang, J. D. Keasling *Nature Chem. Bio.* 2006, 2, 674-681; F. M. Carrau, K. Medina, E. Boido, L. Farina, C. Gaggero, E. Dellacassa, G. Versini, P. A. Henschke, *FEMS Microbio. Lett.* 2005, 243, 107-115).

Within the teipene family, linalool is a particularly intriguing feedstock for fuels due to its molecular structure. Although the RCM of linalool must proceed through a sterically hindered transition state, the reaction is facilitated by coordination of the allylic alcohol. (T. R. Hoye, H. Zhao *Org. Lett.* 1999, 1, 1123-1125). This results in an efficient method for the synthesis of 1-methylcyclopent-2-enol (1) and isobutylene (Scheme 2). Both of these products are of significant interest as they can be converted to renewable fuel and polymer products. Isobutylene is a valuable side-product that can be selectively trimerized to produce jet fuel, dimerized, or alkylated with C4 raffinate to produce high octane gasoline, or polymerized to polyisobutylene. (R. Alcntara, E. Alcintara, L. Canoira, M. J. Franco, M. Herera, A. Navarro, *React. Funct. Polym* 2000, 45, 19-27; J. W. Yoon, S. H. Jhung, T-J. Kim, H-D. Lee, N. H. Jang, J-S. Chang, *Bull. Korean Chem. Soc.* 2007, 28, 2075-2078; D. M. Haskell, F. Floyd, U.S. Pat. No. 4,301,315, 1981; T. I. Evans, L. J. Karas, R. Rameswaran, U.S. Pat. No. 5,877,372, 1999; Y. Li, Y. Wu, L. Liang, Y. Li, G. Wu, Chin. *J. Polym. Sci.* 2010, 28, 55-62; V. Vasilenko, A. N. Frolov, S. V. Kostjuk, *Macromolecules* 2010, 43, 5503-5507; Q. Liu, Yi-X. Wu, Y). Meanwhile, 1 can be efficiently converted to methylcyclopentadiene dimer, which can be hydrogenated and isomerized to produce the high density missile fuel RJ-4. (G. W. Burdette, A. I. Schneider, U.S. Pat. No. 4,398,978, 1983; J. S. Chickos, A. E. Wentz, D. Hillesheim-Cox, *Ind. Eng. Chen. Res.* 2003, 42, 2874-2877 (Scheme 1)).

NMR scale conversions of linalool to 1 under dilute conditions and at elevated temperatures have been reported in the literature. Catalysts used for this reaction (Scheme 3) have included the first generation Grubbs catalyst (2), both a second generation Grubbs (5) and Grubbs-Hoveyda catalyst (4), as well as catalysts with electron withdrawing alkoxides and labile pyridine ligands (6,7). (D. C. Braddock, A. Matsuno, *Tet. Lett.* 2002, 43, 3305-3308; J. C. Conrad, H. H. Parnas, J. L. Snelgrove, D. E. Fogg, *J. Am. Chem. Soc.* 2005, 127, 11882-11883). More recently the RCM of linalool and several other substrates has been studied with ruthenium catalysts functionalized with N-napthyl substituted heterocyclic carbene ligands. (L. Vieille-Petit, H. Clavier, A. Linden, S. Blumentritt, S. P. Nolan, R. Dorta, *Organometallics* 2010, 29, 775-788) Among these examples, the alkoxide functionalized catalysts are particularly notable as they were able to achieve 100% conversion in 15 min at 0.5 mol % loading and in some cases, full conversion in one h at 0.05 mol % loading in refluxing chloroform. This is in contrast to the other catalyst studies that utilized relatively high catalyst loadings (1-5%) to achieve high conversion efficiencies (Table 1). Although these preliminary studies were intriguing, the work in our laboratory focused on maximizing the turnover number (TON) for the RCM of linalool while reducing the use of extraneous solvents and the energy footprint of the process (a key requirement for the synthesis of renewable fuels). To help accomplish this, all of the reactions were run neat, a condition that has been shown to be effective in promoting high TONs for certain substrates. (M. B. Dinger, J. C. Mol, *Adv. Synth. Catal.* 2002, 344, 671-677).

Scheme 3. Structures of selected ruthenium metathesis catalysts that have been studied for the RCM of linalool.

(a: X = OC$_6$H$_5$, X' = F)
(b: X = X' = Cl)
(c: X = Cl, X' = Br)

TABLE 1

Reaction conditions and yield of 1 for a series of ruthenium metathesis catalysts

| Catalyst | Loading (mol %) | Temp | Time | Solvent | Yield |
|---|---|---|---|---|---|
| 2 | 5 | ambient | minutes | CDCl$_3$ | 100 |
| 2 | 0.1 | ambient | 16 h | neat | 0 |
| 2 | 0.1 | 45 | 1 h | neat | 55 |
| 3 | 0.1 | 60 | 30 min | neat | 36 |
| 3 | 0.01 | ambient | 16 h | neat | 0 |
| 3 | 0.01 | 60 | 30 min | neat | 18 |
| 4 | 0.1 | ambient | 45 min | neat | 100 |
| 4 | 0.01 | ambient | 1 h | neat | 44 |

TABLE 1-continued

Reaction conditions and yield of 1 for a series of ruthenium metathesis catalysts

| Catalyst | Loading (mol %) | Temp | Time | Solvent | Yield |
|---|---|---|---|---|---|
| 5, 6, 7a, 7b, 7c | 0.5 | 60 | 15 min | CDCl$_3$ | 100$^b$ |
| 5, 6, 7a, 7b, 7c | 0.05 | 60 | 1 h | CDCl$_3$ | 24, 29, 100, 17, 34 |

As the first step in the development of a large scale synthesis of the high density fuel RJ-4 from a renewable source, the solvent-free, preparative scale RCM of linalool with three commercial catalysts was studied. The first generation Grubbs catalyst 2, a second generation Orubbs catalyst with a sterically open N-heterocyclic carbene ligand 3, and a second generation Grubbs-Hoveyda catalyst 4 were screened for activity. For catalyst 2, attempts to decrease the loading to 0.1 mol % resulted in incomplete conversion to the alcohol. No reaction was observed at room temperature, while reaction at 45° C. resulted in 55% conversion after one hour. Increasing the reaction time did not lead to further reaction. Catalyst 3 which was chosen based on its well established activity in the RCM of sterically hindered substrates produced no discernible product after 16 h at ambient temperature with either 0.1 or 0.01 mol % loading, however at 60° C., yields of 36 and 18% were obtained, respectively. Unfortunately, catalyst 3 deactivated within 30 minutes at this temperature, a result that was not surprising given the reported modest thermal stability of this catalyst. (I. C. Stewart, T. Ung, A. A. Pletnev, J. M. Berlin, R. H. Grubbs, Y. Schrodi, *Org. Lett.* 2007, 9, 1589-1592).

Figure 1:
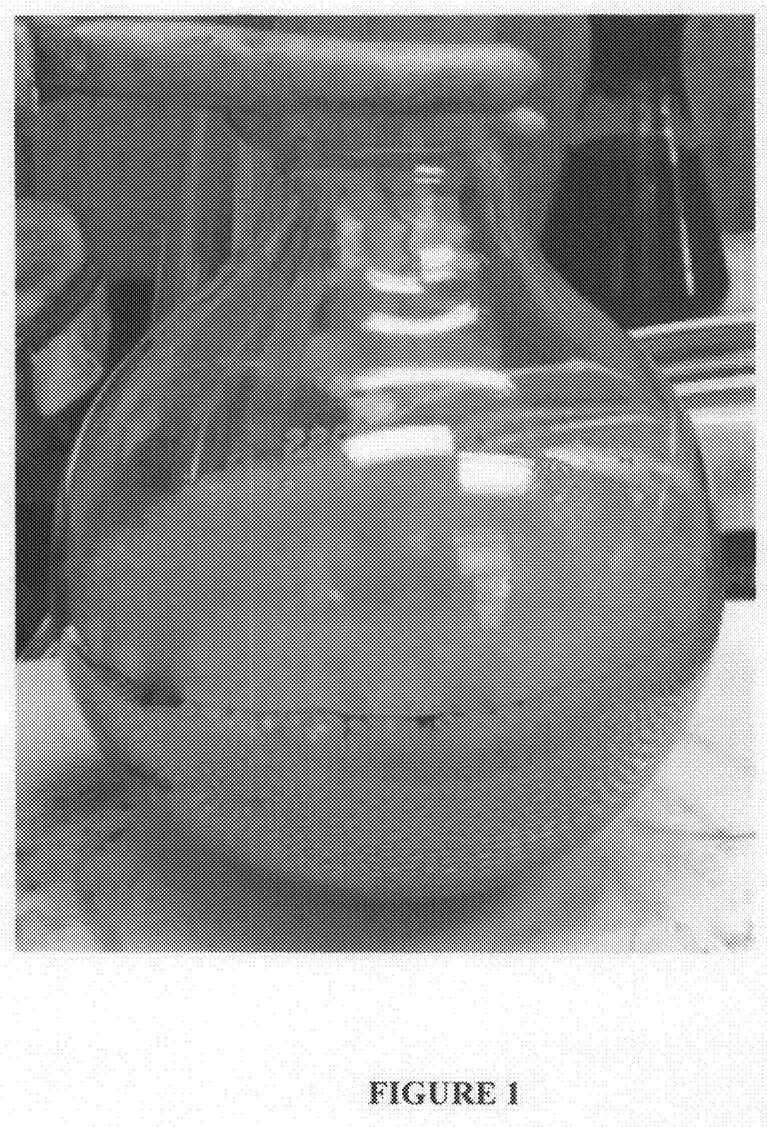
FIG. 1 is a photograph of the room temperature, solvent free reaction of linalool with catalyst at five minutes after addition, according to embodiments of the invention.

FIG. 1 is a photograph of the room temperature, solvent-free reaction of linalool with catalyst 4 at five minutes after addition. Vigorous bubbling is due to production of isobutylene. To improve the conversion efficiency, the more stable catalyst 4 was evaluated at a loading of 0.1 mol %. At room temperature the reaction proceeded rapidly (FIG. 1) with copious production of isobutylene. By this method linalool was converted quantitatively to 1 in 45 min at ambient temperature. At 0.01 mol % loading, a 44% conversion to the alcohol was achieved in one h, representing a remarkable TON of 4400. Reaction for longer periods of time resulted in no improvement in yield. Based on the catalyst screening, 4 was utilized in preparative scale (30 g) syntheses of 1. Isobutylene was either collected with a dry ice condenser or allowed to escape through a bubbler. At the conclusion of the reaction, the product was isolated by vacuum distillation at room temperature; yields of >95% were routinely achieved.

In an attempt to improve the conversion efficiencies of catalysts 2 and 4, the effect of increasing the temperature was studied. Interestingly, when either 2 or 4 were used as the catalyst, a reaction temperature of 60° C. resulted in partial conversion of 1 to methylcyclopentadiene (MCPD). GC/MS analysis of the reaction mixture showed that linalool had been converted to a complex mixture of 1, cyclopentenol ethers, MCPD, and methylcyclopentadiene dimers (Scheme 4). In effect it appeared that 2 and 4 were acting as dehydration catalysts. Interestingly, for 4, this same effect was not observed when sufficient linalool was present in solution. As a control, a 0.01 mol % solution of catalyst 4 in linalool was prepared. After the reaction had proceeded to 44% conversion, the mixture was heated to 60° C. for 16 h. No dehydration of the product was observed. It is also important to note that catalyst decomposed through air exposure was not active for the dehydration of the alcohol. Rapid stirring of the flask in open air or alternatively active bubbling of air into the reaction flask resulted in a color change from green to brown-black. This oxidized mixture was much less prone to dehydration reactions.

Although the dehydration reaction appeared to be mediated by the ruthenium catalyst, another possibility is that the catalyst reacted with linalool, 1, or water to exchange alkoxide or hydroxide ligands with the chloride ligands. This process would release catalytic amounts of HCl which could then lead to dehydration of the alcohol. To investigate the extent to which a Lewis acid would dehydrate 1, the alcohol was allowed to react with the Lewis acids $PdCl_2(PhCN)_2$ and $Ru(COD)Cl_2$ at room temperature in $CDCl_3$. As a control, Pd(0) (5% Pd/C) was also evaluated as a catalyst for the dehydration of 1. Interestingly, all of the catalysts converted 1 to similar mixtures of dehydrated products comparable to those observed with the metathesis catalysts. Further observation revealed that although neat samples of 1 were stable indefinitely in closed flasks at room temperature, NMR samples in $CDCl_3$ slowly converted to dehydrated mixtures, albeit at a much slower rate than for the Lewis acid catalyzed reactions. Given the known decomposition of chloroform to produce HCl and phosgene, it seems likely that even this small amount of acid was sufficient to promote the dehydration of the alcohol.

Scheme 4. Mechanism for the acid catalyzed dehydration of 2-methyl-1-cyclopentenol.

Although the Ru-catalysts showed some modest activity for the partial dehydration of 1, more efficient and selective methods were sought to convert 1 to MCPD. Given the rapid room temperature conversion of MCPD to dimer, particularly in the presence of acid catalysts, two distinct routes to the dimer were conceived. In the first route, a solid acid catalyst would be employed and the dehydration and dimerization would occur in the same flask. In the second route, a dehydration catalyst of much lower acidity would be employed and the reaction carried out under reduced pressure, allowing the volatile MCPD to be easily separated from the reaction mixture. For the first route, heterogeneous solid acid catalysts were employed to allow for easy isolation of the product Montmorillonite K10 (MMT-K10), an acid clay, and Nafion SAC-13, a silica supported perfluorinated cation exchange resin were screened for activity. Although both catalysts resulted in high conversions (95% conversion in one hour at ambient temperature), both yielded complex mixtures consisting of ether, dimer, significant amounts of trimer, and other heavier oligomers (Table 2). To try and trap MCPD prior to oligomerization, the reaction was conducted with Nation SAC-13 at 40° C. under reduced pressure (40 torr). Although the isolated MCPD was >90% pure, the yield was low and the reaction mixture rapidly oligomerized to a thick orange oil composed of heavy oligomers. From this result it was clear that in the case of strong heterogeneous acid catalysts, oligomerization occurred more rapidly than MCPD could be removed from the reaction flask.

To further investigate optimal dehydration conditions, a series of weak Bronsted and Lewis acid catalysts were screened to determine their activity in the selective dehydration of 1 (Table 2). Benzoic acid and dilute HCl were unselective and produced primarily ether along with dimer and trimer. Surprisingly, $Pd(COD)Cl_2$ reacted almost quantitatively and produced 66% dimer along with significant amounts of trimer and tetramer. In the search for a milder dehydrating agent, magnesium sulfate was employed as a catalyst and produced only ethers. In contrast to the other dehydration catalysts that produced primarily one ether isomer, $MgSO_4$ produced the two distinguishable ether isomers in nearly equal amounts. This difference in isomer distribution is attributed to the lack of suitable acid sites on the catalyst. In the absence of these sites the reaction is driven by the coordination of water to magnesium cations and is dependent on the auto-ionization of the alcohol. Based on these initial screening results, an aluminum phosphate catalyst was prepared and evaluated as a dehydration catalyst. (A. W. Wang, Final Report US Department of Energy, Contract No. DE-FC22-94PC93052, 2002). Under a variety of conditions, this catalyst was selective for the production of only ethers, MCPD, and dimers; no heavier oligomers were formed. Despite the favorable product distribution, the conversion efficiency of this catalyst was limited by the production of water in the dehydration reaction. To overcome this hurdle, mixtures of $AlPO_4$ with a suitable drying agent were employed. An $AlPO_4$/molecular sieve catalyst resulted in a low overall yield of MCPD with formation of an oligomeric mixture. In contrast, an $AlPO_4/MgSO_4$ catalyst permitted the direct conversion to MCPD. The optimized catalyst allowed for a 78% isolated yield of isomeric MCPD from 1.

TABLE 2

Catalysts for the dehydration of 1

| Catalyst | Temp | Time | Pressure | Products 1:ether:dimer: oligomer |
|---|---|---|---|---|
| MMT-K10 | 25 | 1 h | atm | 5:41:22:32 |
| Nafion SAC-13 | 25 | 1 h | atm | 6:35:23:36 |
| Pd(COD)Cl$_2$ | 25 | 16 h | atm | <1:14:66:23 |
| 2M HCl | 25 | 1 h | atm | 0:(86):13$^a$ |
| MgSO$_4$ | 25 | 16 h | atm | 16:84:0:0 |
| Benzoic Acid | 25 | 16 h | atm | 8:66:21:4 |
| AlPO$_4$/MgSO$_4$ | 60 | 5 h | 40 torr | 10:90:0:0$^b$ |

$^a$The number in parantheses is the mass % of ethers and dimers combined.
$^b$This distribution represents what was left in the reaction flask. A 78% isolated yield of MCPD isomers was obtained through this method.

Figure 2:
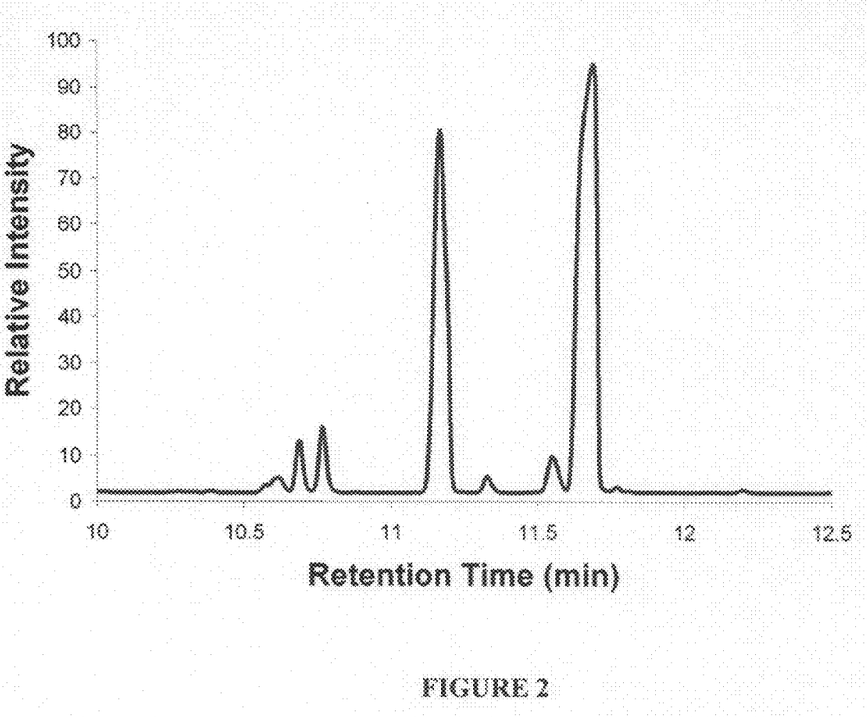
FIG. 2 is a graph illustrating a GC Chromatogram of MCPD dimers derived from dehydration of 1 with $AlPO_4$/$MgSO_4$ followed by ambient temperature dimerization, according to embodiments of the invention.

FIG. 2. GC Chromatogram of MCPD dimers derived from dehydration of 1 with $AlPO_4/MgSO_4$ followed by ambient temperature dimerization.

The dimer product distribution resulting from the room temperature Diels-Alder cycloaddition of MCPD is of significant interest and is in-part controlled by the starting composition of MCPD isomers. Dehydration of the alcohol with $AlPO_4$ at 60° C. yields 84% 2-methylcyclopentadiene (8) and 16% 1-methylcyclopentadiene (9), while 5-methylcyclopentadiene was not observed. The predominance of 8 results from the formation of a more stable tertiary carbocation compared to the secondary carbocation intermediate required for 9 (Scheme 4). In commercial methylcyclopentadiene dimer, seven peaks are observed in the gas chromatogram. (M. A. Diez, M. D. Guillen, C. G. Blanco, J. Bermejo, *J. Chromatography* 1990, 508, 363-374.) The distribution contains four major peaks representing various isomers resulting from the cycloaddition of 2-methyl and 1-methyl cyclopentadiene. The dimers are present almost exclusively as the endo isomers. In the current work, seven peaks are observed, however the distribution is significantly different than for the commercial product, with two peaks representing 88% of the dimers. The largest peak (56%) is observed for 3,9-dimethyl-ecndo-tricyclo[5.2.1.0$^{2,6}$]deca-3,8-diene (10), while the other main peak (33%) is observed for 4,9-dimethyl-endo-tricyclo[5.2.1.0$^{2,6}$]deca-3,8-diene (11) (Scheme 5). In comparison, the commercial product is 36% 10 and 29% 11. (W. Thommen, H. Pamingle, K. H. Schulte-Elte. *Helv. Chim. Acta* 1989, 72, 1346-1353). Coupling of two molecules of 8 yields 10, while coupling of 8 and 9 yields 11. The distribution of isomers is also dependent on both the relative dimerization rates of 8 and 9 as well as concomittant monomer isomerization. Previous studies have shown that 2-methylcyclopentadiene dimerizes faster than 1-methylcyclopentadiene ostensibly due to less steric crowding at the site of cycloaddition; this effect further influences the final distribution. (S. M. Csicsery *J. Org. Chem.* 1960, 25, 518-521).

Interestingly, dimer 12 which represents roughly 10% of commercial dimethyldicyclopentadiene is only 3% of the current mixture. This is likely the result of the known [3,3]-sigmatropic Woodward-Katz rearrangement to 11 being catalyzed by the dehydration conditions. (W. Thommen, H. Pamingle, K. H. Schulte-Elte, *Helv. Chim. Acta* 1989, 72, 1346-1353).

Scheme 5. Prominent endo-isomers produced from the thermal dimerization of MCPD isomers derived from 2-methyl-1-cyclopentenol. The first number of a pair represents the % composition produced in this work, while the numbers in brackets refer to % composition of the commercial product.

Scheme 6.

In order to convert the dimer mixture to RJ-4, it must first be hydrogenated. This was accomplished under mild conditions (40 psi, $PtO_2$ catalyst) and resulted in six distinguishable isomers. The four major peaks representing 91% of the product are the four sets of diasteriomers arising from the nonsterospecific hydrogenation of 10 and 11. After hydrogenation, these mixtures can be isomerized with strong Lewis acid catalysts to fuels rich in exo-isomers.

In summary, a highly efficient and selective synthesis for the conversion of linalool to specialized fuel products has been developed. The optimized approach offers a high catalyst turnover number, solvent free conditions, low external energy demands, and an exceptionally well defined product distribution. Further work to effectively reduce catalyst loadings and to establish how the distribution of dimers will affect the performance of high density fuel mixtures is ongoing.

EXPERIMENTAL SECTION

General: Grubbs 1$^{st}$ generation catalyst (2), Grubbs 2nd generation catalyst (3), and Grubbs-Hoveyda 2$^{nd}$ generation catalyst (4), were purchased from Aldrich, stored in a nitrogen filled glove box, and used as received. Linalool (97%, FG) was purchased from Aldrich and was distilled under reduced pressure and stored under nitrogen before use unless otherwise noted. $MgSO_4$ (Polarchem), 4 Å molecular sieves (Aldrich), MMT-K10 (Aldrich), Nafion SAC-13 (Aldrich), benzoic acid (Aldrich), $Al(NO3)_3$-$9H_2O$ (RG Aldrich), $H_3PO_4$ (85%, Fisher), and $NH_4OH$ (27%, Aldrich) were used as received. $^1$H NMR measwuments were performed using a Bruker AC 200 instrument. $^1$H NMR chemical shifts are reported versus the deuterated solvent peak ($CDCl_3$, δ 7.25 ppm). Product mixtures were analyzed with an Agilent 6890-OC system with a Restek RTX-5MS 30-meter column. The GC inlet temperature was 250° C. and the column oven temperature was initially held at 40° C. for three minutes and then increased to 350° C. at 10° C./min. An Agilent mass selective detector (MSD) 5973 system was used to identify the sample's components.

Figure 3:
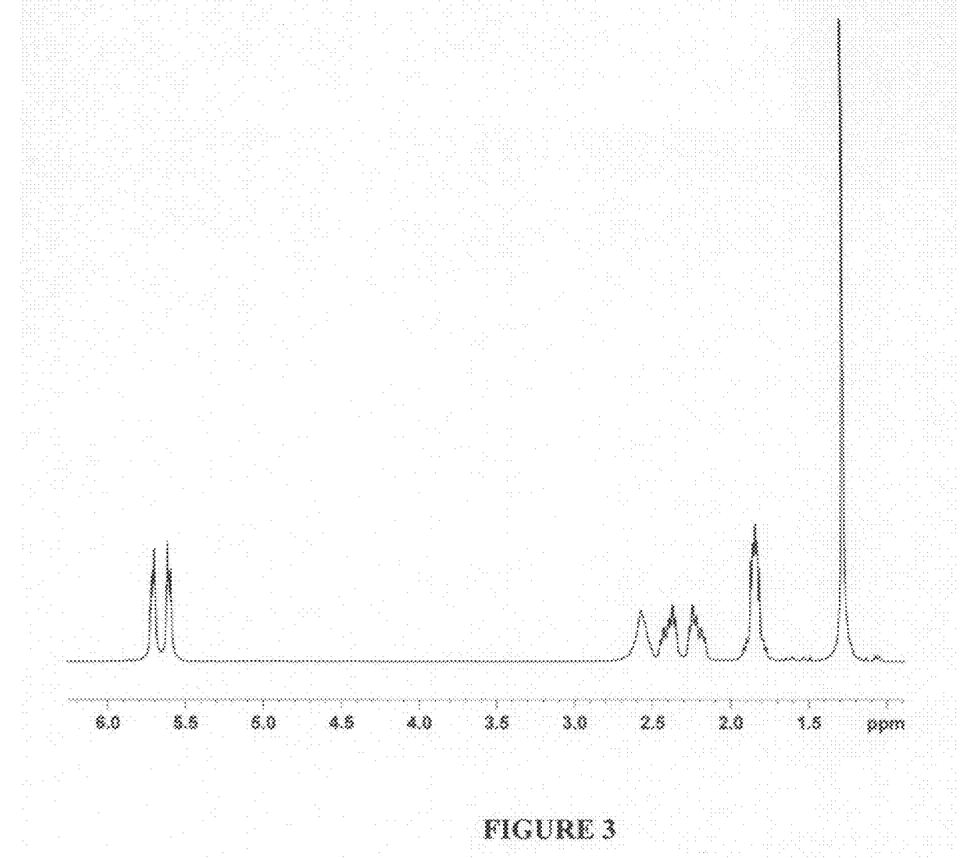
FIG. 3 is a graph that is a representative $^1H$ NMR of 1-methylcyclopent-2-enol produced by RCM of linalool, according to embodiments of the invention.

Example 1, general preparative scale procedure for synthesis of 1 from linalool: Reactions were run with 0.1 mol % of the Hoveyda-Grubbs $2^{nd}$ generation catalyst. The catalyst was stored in the glove box and the required amount was removed in a round bottom flask charged with a stirbar, and sealed with a septum. Linalool was transferred via syringe into the RBF containing the catalyst. At this point the flask was vented through an oil bubbler and within 30 seconds vigorous bubbling began while stirring at room temperature. The bubbling continued for 30-45 minutes and then ceased. Once bubbling had stopped air was bubbled into the reaction mixture for 15 minutes to ensure the catalyst was inactive. $^1$H NMR of the crude reaction mixture showed 100% conversion of starting linalool. The product was immediately vacuum transferred (1 torr) to a chilled flask (−78° C.). After transfer the product was sealed under nitrogen and stored at room temperature. The product was analyzed via NMR. $^1$H NMR (CDCl$_3$) δ: 1.29 (s, 3H), 1.84 (m, 2H), 2.23 (m, 1H), 2.37 (m, 1H), 2.57 (broad s, 1H), 5.65 (m, 214). FIG. 3. Representative $^1$H NMR of 1-methylcyclopent-2-enol produced by RCM of linalool.

Figure 4:
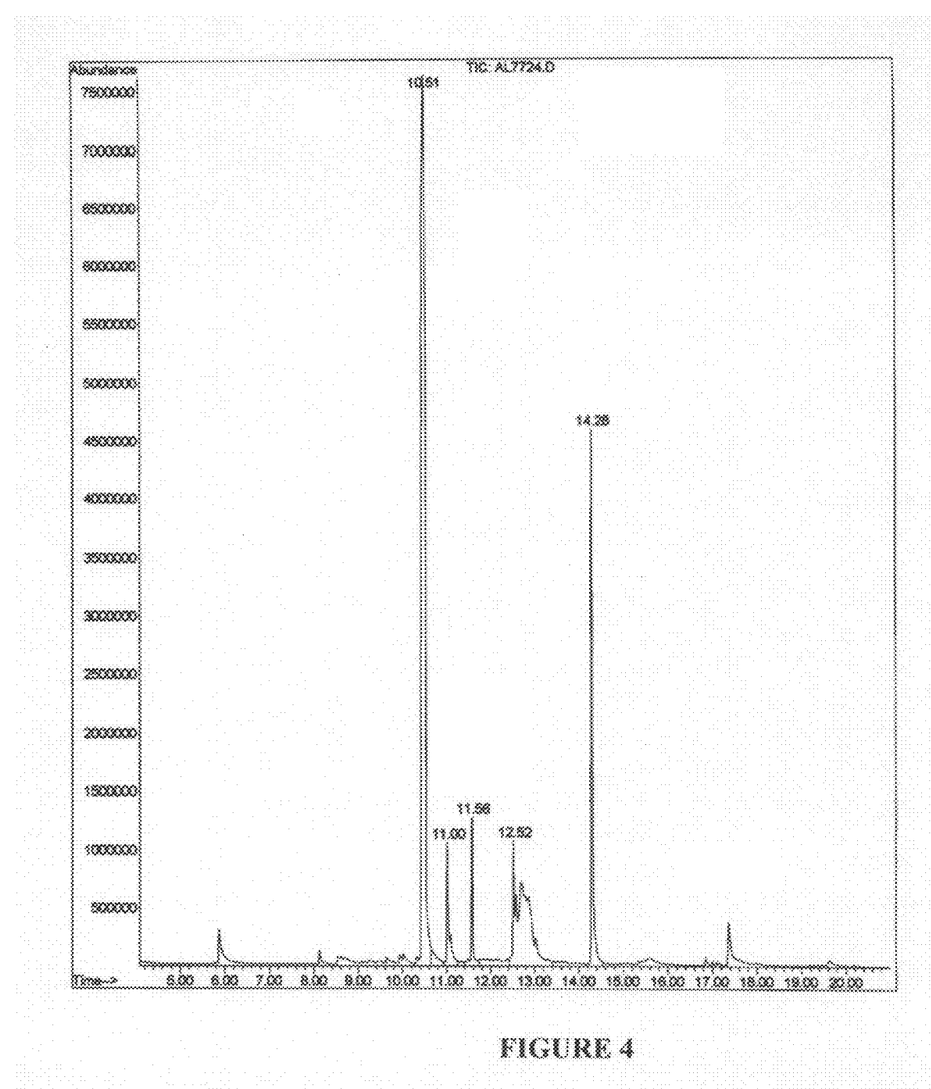
FIG. 4 is a graph showing a representative GC of the mixture in the reaction flask after RCM with Grubbs $1^{st}$ generation catalyst, according to embodiments of the invention.

Example 2, RCM with Grubbs' $1^{st}$ generation catalyst (2): Grubbs' $1^{st}$ generation catalyst (2) (26 mg, 0.1 mol %) was placed in a 25 mL round bottom flask charged with a Teflon stirbar. The flask was sealed with a septum and removed from the glove box. The flask was placed in an oil bath and held at 45° C. To this flask 5 mL of distilled linalool was added via syringe and the reaction was vented to an oil bubbler. Within 5 minutes slow bubbling was seen in the oil bubbler, but no bubbling was seen in the reaction flask. At 45 minutes bubbling began in the reaction flask and ceased completely at 90 min. $^1$H NMR showed 55% conversion of the starting linalool. FIG. 4. A representative GC of the mixture in the reaction flask after RCM with Grubbs $1^{st}$ generation catalyst. The peak with RT=10.51 represents unreacted linalool. Significant dehydration products are present with very little methylcyclopentenol (RT-6 min) present.

Example 3, RCM with $2^{nd}$ generation Grubbs (3): $2^{nd}$ generation Grubbs catalyst (3) (12 mg, 0.1 mol %) was placed in a 25 mL round bottom flask charged with a Teflon stirbar. The flask was sealed with a septum and removed from the glove box. The flask was placed in an oil bath and held at 60° C. To this flask, 3 mL of distilled linalool was added via syringe and the reaction was vented to an oil bubbler. Within 5 minutes bubbling was seen in the flask and this continued for 20 minutes after which bubbling ceased. $^1$H NMR taken at 30 min showed 36% conversion of the starting linalool. A spectrum at 3 h showed no further conversion.

Example 4, dehydration catalyst screening: Unless otherwise noted all of the dehydration test reactions were carried out at room temperature with stirring in air. The dehydrating agent was added to 1 mL of 1 in a vial and stirred. Crude products were analyzed by $^1$H NMR and GC-MS.

Nafion SAC-13: 50 mg of Nafion Sac-13 was added and the reaction was stirred for 1 h. $^1$H NMR showed only a small amount of the starting alcohol and no methylcyclopentadiene. Analysis by GC-MS gave 6% 1, 35% ethers, 23% dimers, 28% trimers and 9% tetramers.

MMT-K10: 50 mg of MMT-K10 was added and the reaction was stirred for 1 h. $^1$H NMR showed only a small amount of the starting alcohol and no methylcyclopentadiene. Analysis by GC-MS gave 5% 1, 41% ethers, 22% dimers, 28% trimers and 4% tetramers.

HCl: 1 mL of 2M HCl was added and the reaction was stirred for 1 hour. $^1$H NMR at 1 h showed no starting alcohol and no methylcyclopentadiene. Analysis by GC-MS gave a complex mixture of ethers, and dimers making up 86% of the sample with an additional 12% trimers and 1% tetramers.

Benzoic Acid: 50 mg of benzoic acid was added and the reaction was stirred for 1 hour. The NMR showed no reaction at 1 hour and the solution was left to stir overnight. $^1$H NMR at 20 h showed only a small amount of the starting alcohol, and no methylcyclopentadiene. Analysis by GC-MS gave 8% 1, 66% ethers, 22% dimers and 4% trimers.

Magnesium Sulfate: 150 mg of MgSO$_4$ was added and the reaction was stirred for 1 h. $^1$H NMR showed no reaction and the mixture was left to stir overnight. $^1$H NMR at 24 h showed significant amounts of the starting alcohol, and no methylcyclopentadiene; the reaction was stopped at this point. Analysis by GC-MS gave 16% 1 and 84% ethers. No conversion to methylcyclopentadiene or heavier products was observed.

Pd(COD)C$_2$: 50 mg of Pd(COD)Cl$_2$ was added and the reaction was stirred for 1 h; $^1$H NMR taken at this point showed no significant conversion and the solution was left to stir overnight. $^1$H NMR at 24 hours showed no starting alcohol, and no methylcyclopentadiene. Analysis by GC-MS gave <1% 1, 14% ethers, 66% dimers, 16% trimers, and 7% tetramer.

Aluminum Phosphate with 4 Å Mol. Sieves: 310 mg of AlPO$_4$ and 500 mg of 4 Å molecular sieves were added. This flask was placed in a 60° C. oil bath and 6 mL of 1 was added via syringe. The desired methylcyclopentadiene was obtained through distillation under vacuum (~40 torr). The receiving flask was placed in dry ice to ensure no loss of product. The reaction ran for 8 hours and only ~100 μL was collected in the receiving flask. $^1$H NMR of this portion showed a mixture of 1-methylcyclopentadiene and 2-methylcyclopentadiene in a 1:3 ratio, respectively. The reaction flask was a thick orange oil and was not analyzed farther.

Example 5, preparation of AlPO$_4$: This synthesis was adapted from a literature procedure. Aluminum nitrate nonahydrate, Al(NO$_3$)$_3$.9H$_2$O, (16.0 g, 43 mmol) was dissolved in 75 mL of DI water. 3 mL of 85% H$_3$PO$_4$ was added dropwise with rapid stirring. 13 mL of 27% NH$_4$OH was diluted in 30 mL of DI water and then this diluted solution was slowly added dropwise to the reaction mixture. Once addition was complete a thick white precipitate had formed and an additional 20 mL of DI water was added to allow for continued stirring of the mixture. The slurry was left to stir for 20 hours after which time the solution was filtered. The resulting solid was re-dispersed in 100 mL of DI water and stirred for 1 hour. The mixture was then centrifuged and the water was decanted. The solid was dried overnight at 120° C. in a vacuum oven. The white solid was powdered using a mortar and pestle to yield 4.78 g of white solid.

Example 6, dehydration with AlPO$_4$ & MgSO$_{4:\ AlPO4}$ (1.34 g, 11 mmol) and MgSO$_4$ (1.63 g, 13 mmol) were placed in a 50 mL round bottom flask charged with a stirbar. To this flask 1 (13.01 g, 0.13 mol) was added, and the flask was fit with a small distillation head. The receiving flask was placed in a dry ice bath and the reaction was placed under vacuum (40 torr). The reaction was run at 60° C. for 5 hours. Total yield of the distillate was 78%. $^1$H NMR for the major product, 2-methylcyclopentadiene (CDCl$_3$) δ: 2.06 (s, 3H), 2.98 (s, 1H), 6.04 (s, 1H), 6.44 (s, 2H).

Figure 5:
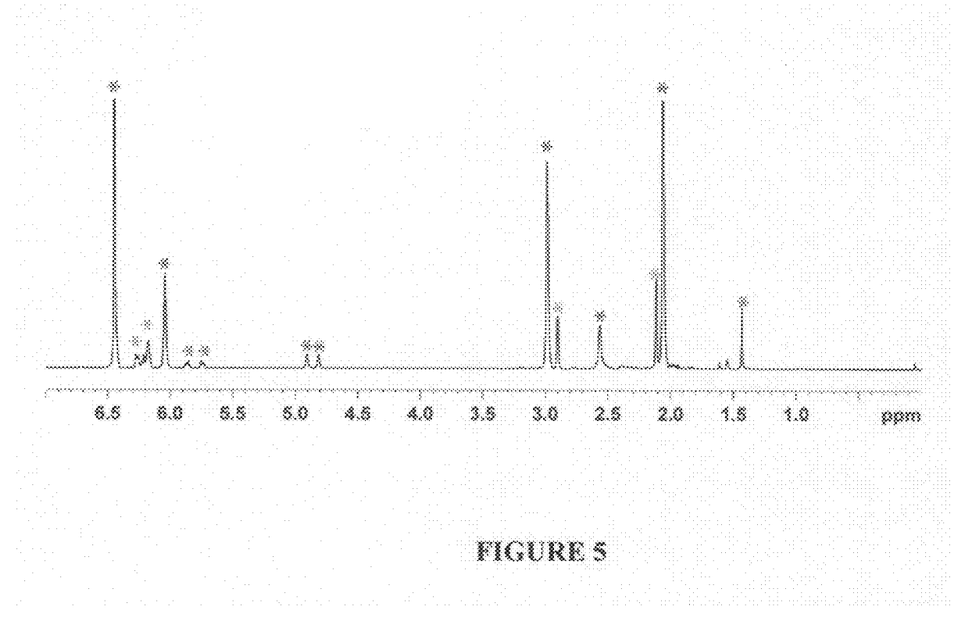
FIG. 5 is a graph showing a representative $^1H$ NMR of the 2-methylcyclopentadiene product from the RCM reaction, minor products include 1-methylcyclopentadiene, methyl cyclopentadiene dimer, and starting alcohols and ethers, according to embodiments of the invention.
Figure 6:
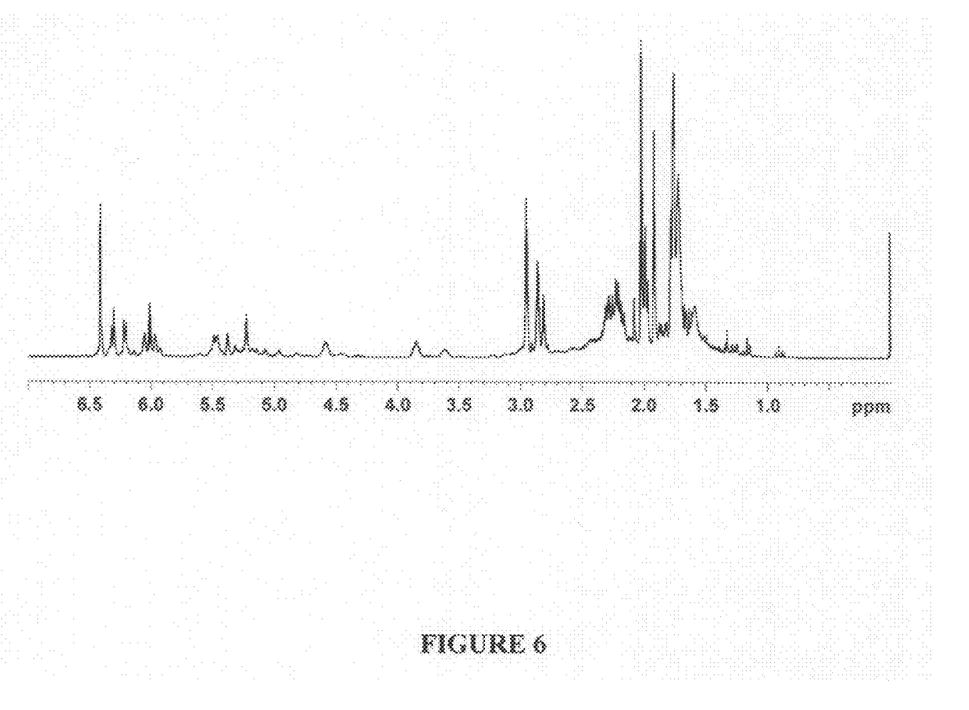
FIG. 6 is a graph showing a representative $^1H$ NMR spectrum of the dehydration of 1 with the heterogeneous acid catalyst, Nafion SAC-13, according to embodiments of the invention.
Figure 7:
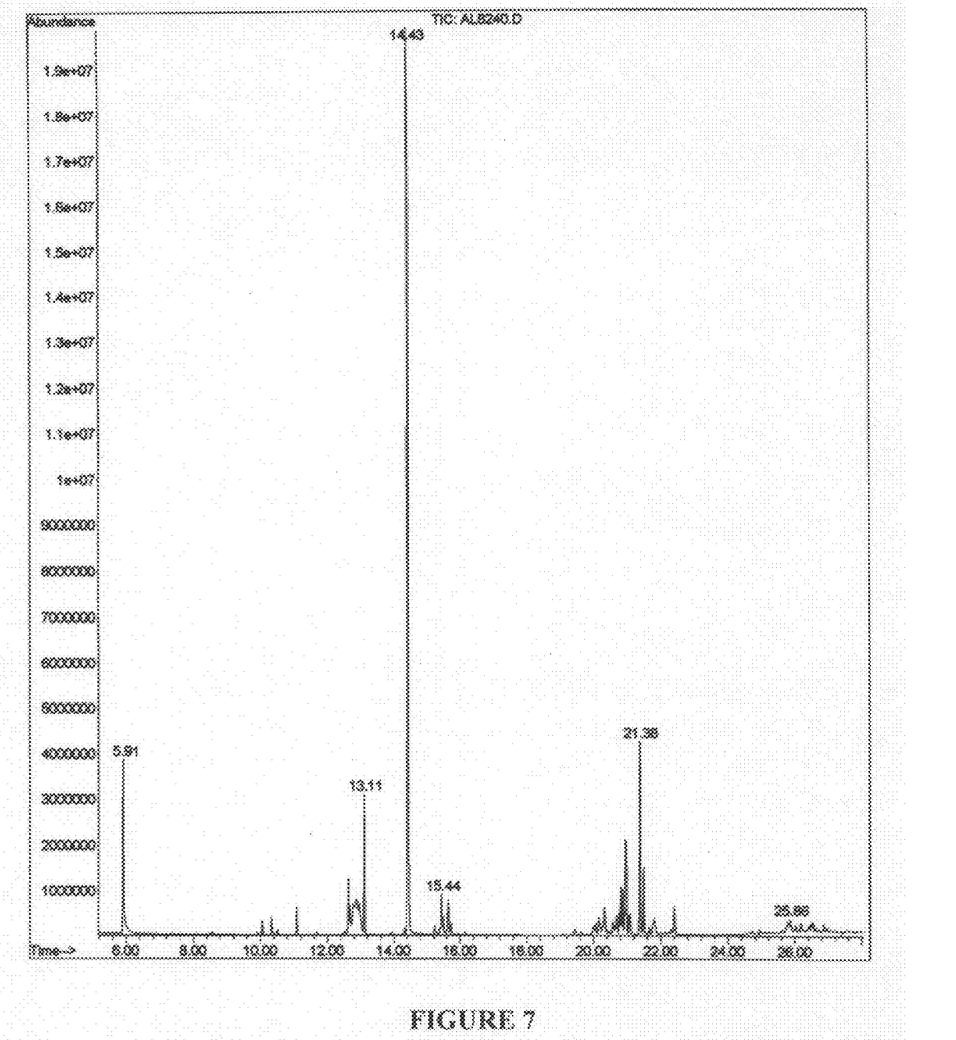
FIG. 7 is a graph showing a representative GC from the reaction flask after dehydration with Nafion SAC-13 shows starting material, ethers, dimers, trimers, and tetramers in solution, according to embodiments of the invention.
Figure 8:
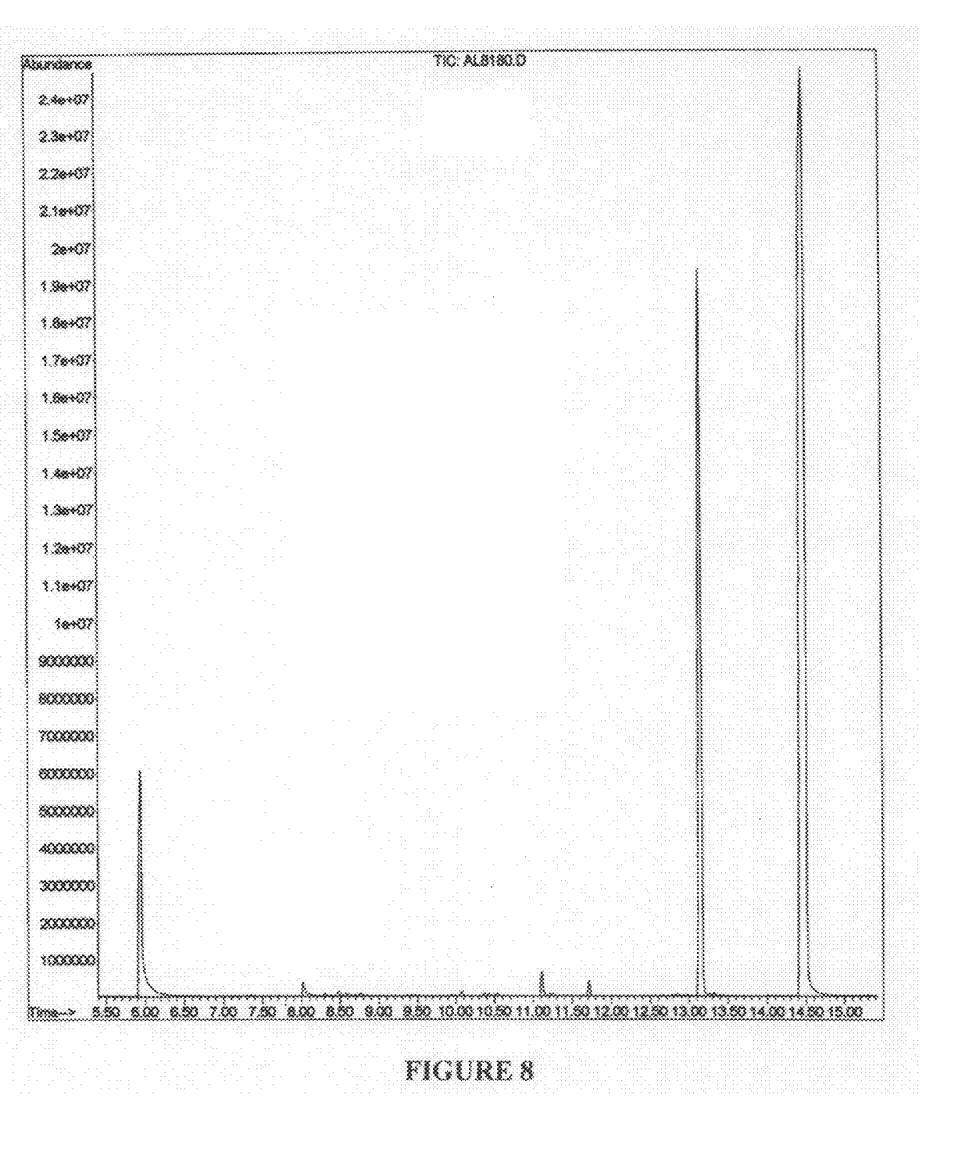
FIG. 8 is a graph showing a representative GC from the reaction flask after dehydration with $AlPO_4$, according to embodiments of the invention.

FIG. 5. Representative $^1$H NMR of the 2-methylcyclopentadiene product from the RCM reaction, minor products include 1-methylcyclopentadiene, methyl cyclopentadiene dimer, and starting alcohols and ethers. FIG. 6. A representative $^1$H NMR spectzm of the dehydration of I with the heterogeneous acid catalyst, Nafion SAC-13. FIG. 7. A representative GC from the reaction flask after dehydration with Nafion SAC-13 shows starting material, ethers, dimers, trimers, and tetramers in solution. FIG. 8. A representative GC from the reaction flask after dehydration with AlPO$_4$. The only major peaks observed are for starting material and ethers; no heavier product formation is observed.

Figure 9:
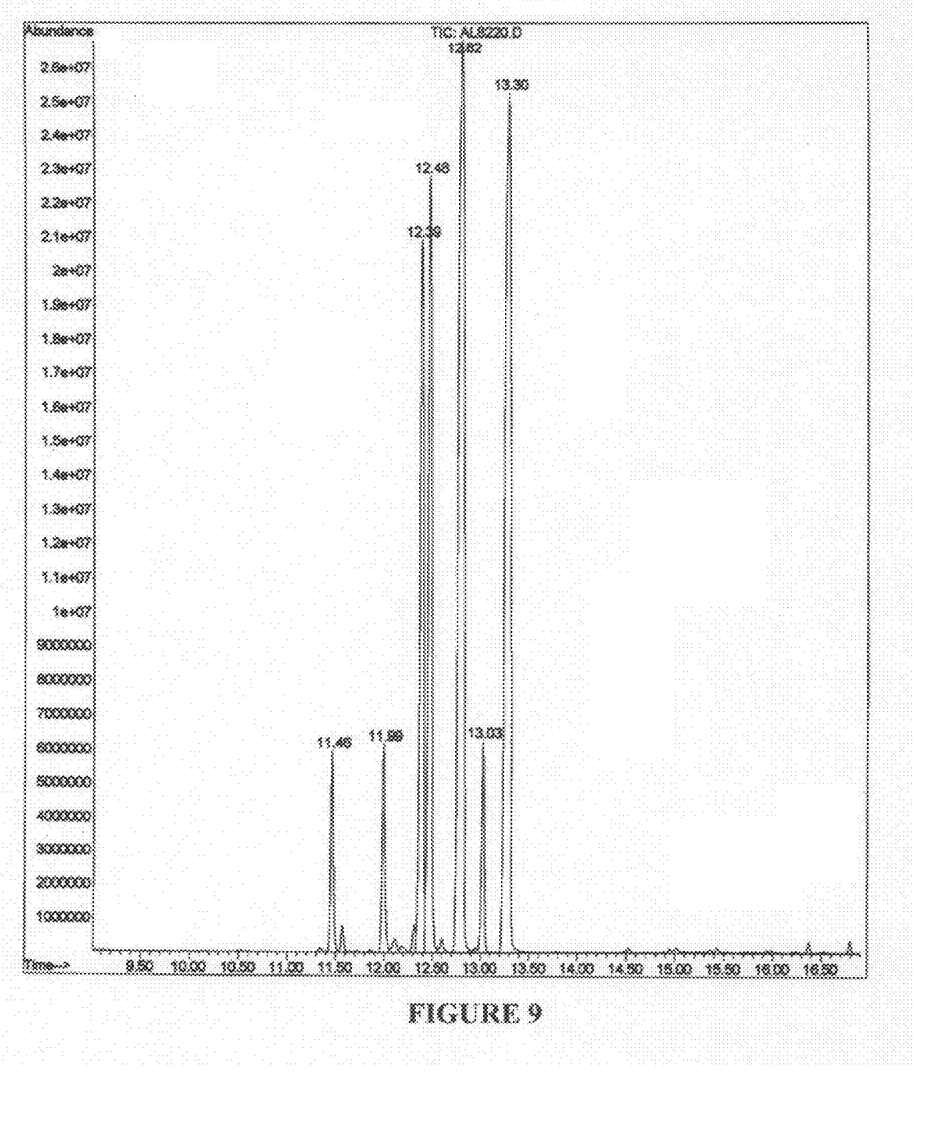
FIG. 9 is a graph showing a GC of the dimer mixture after hydrogenation with $PtO_2$ at 40 psi $H_2$, according to embodiments of the invention.

Example 7, hydrogenation of MCPD dimers 8 g (0.1 mol) of MCPD dimers were diluted with 20 mL THF. PtO$_2$ (80 mg, 0.35 mmol) was added to the mixture which was then transferred to a small Parr hydrogenation apparatus under 40 psi 1H$_2$ with shaking. The pressure was monitored and held between 30-40 psi for the duration of the reaction. After 20 hours H$_2$ was no longer being consumed and the reaction was stopped. The excess H$_2$ was removed under reduced pressure and the platinum catalyst was removed by filtration through a plug of glass wool. THF was removed under reduced pressure to yield a mixture of hydrogenated MCPD dimers which were subsequently analyzed by GC-MS. FIG. 9. GC of the dimer mixture after hydrogenation with PtO$_2$ at 40 psi H$_2$.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for manufacturing high density fuels, comprising:
    reacting at least one terpene alcohol with at least one Ru-metathesis catalysts with a solvent or under solvent-free conditions to produce 1-methylcyclopent-2-enol and isobutylene;
    continuously separating said isobutylene by distillation;
    dehydrating said 1-methylcyclopent-2-enol with at least one heterogeneous dehydration catalyst to produce a mixture consisting of 2-methyl cyclopentadiene and 1-methyl cyclopentadiene;
    thermal dimerizing said methylcyclopentadienes to produce a mixture of methylcyclopentadiene dimers comprising greater than 50% 3,9-dimethyl-endo-tricyclo [5.2.1.0$^{2,6}$]deca-3,8-diene and about 30% 4,9-dimethyl-endo-tricyclo [5.2.1.0$^{2,6}$]deca-3,8-diene;
    hydrogenating said methylcyclopentadienes dimers with at least one hydrogenation catalyst to produce hydrogenated methylcyclopentadienes dimers; and
    isomerizing said hydrogenated methylcyclopentadienes dimers with at least one Lewis acid catalyst to produce high density fuels.

2. The method according to claim 1, wherein said at least one terpene alcohol is linalool.

3. The method according to claim 1, wherein said at least one Ru-metathesis catalysts comprises of first generation Grubbs catalyst, second generation Grubbs, Grubbs-Hoveyda catalyst, catalysts with electron withdrawing alkoxides and labile pyridine ligands, heterogeneous metal oxides, and polymer supported catalysts.

4. The method according to claim 1, wherein said at least one heterogeneous dehydration catalyst is selected from the group consisting of AlPO$_4$, Al$_2$O$_3$, SiO$_2$, MgSO$_4$, and zeolites.

5. The method according to claim 1, wherein said thermal dimerizing method comprises increasing the temperature to accelerate the dimerization of said methylcyclopentadienes to produce methylcyclopentadiene dimers.

6. The method according to claim 1, wherein a Lewis acid catalyst is employed to increase the rate of dimerization of methylcyclopentadienes.

7. The method according to claim 1, wherein said thermal dimerizing method comprises conducting the dimerization at room temperature.

8. The method according to claim 1, wherein said at least one hydrogenation catalyst includes at least one of Ni, Pd, Pt, and Cu, either supported or unsupported.

9. The method according to claim 1, wherein said at least one Lewis acid catalyst is selected from the group consisting of AlCl$_3$, ionic liquids or salts including AlCl$_4^-$ as the anion.

10. The method according to claim 1, wherein said high density fuels is tetrahydromethyl-cyclopentadiene dimmer (RJ-4).

11. A high density fuel produced by the methods of claim 1.

* * * * *